US009583323B2

(12) United States Patent
Tate et al.

(10) Patent No.: US 9,583,323 B2
(45) Date of Patent: Feb. 28, 2017

(54) USE OF VARIABLE XIC WIDTHS OF TOF-MSMS DATA FOR THE DETERMINATION OF BACKGROUND INTERFERENCE IN SRM ASSAYS

(75) Inventors: Stephen A. Tate, North York, CA (US); David M. Cox, Barrie, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 573 days.

(21) Appl. No.: 14/123,185

(22) PCT Filed: May 30, 2012

(86) PCT No.: PCT/IB2012/001049
§ 371 (c)(1),
(2), (4) Date: Nov. 29, 2013

(87) PCT Pub. No.: WO2012/164375
PCT Pub. Date: Dec. 6, 2012

(65) Prior Publication Data
US 2014/0095084 A1    Apr. 3, 2014

Related U.S. Application Data

(60) Provisional application No. 61/493,352, filed on Jun. 3, 2011.

(51) Int. Cl.
*H01J 49/02* (2006.01)
*H01J 49/00* (2006.01)
*G06F 19/00* (2011.01)

(52) U.S. Cl.
CPC ............ *H01J 49/02* (2013.01); *G06F 19/703* (2013.01); *H01J 49/0031* (2013.01)

(58) Field of Classification Search
CPC ...... H01J 49/02; H01J 49/0031; G06F 19/703
See application file for complete search history.

(56) References Cited

U.S. PATENT DOCUMENTS 8,809,770 B2 *  8/2014  Bonner ............... H01J 49/0031
                                                   250/281
2007/0231909 A1 * 10/2007  Hunter ............... G01N 33/6848
                                                   436/15

(Continued)

FOREIGN PATENT DOCUMENTS

WO    2005/079263 A2    9/2005
WO     200905491 A2     8/2009

*Primary Examiner* — John Breene
*Assistant Examiner* — Mohammad Islam
(74) *Attorney, Agent, or Firm* — John R. Kasha; Kelly L. Kasha; Kasha Law LLC (57) ABSTRACT

Systems and methods identify a product ion that does not include an interference. A full product ion spectrum for a mass range of an analyte in a sample is received from a tandem mass spectrometer. A first set of one or more peak parameters is calculated for a product ion in the full product ion spectrum using a first XIC window width. A second set of one or more peak parameters is calculated for the product ion using a second XIC window width. The product ion is identified as not including an interference, if the first set of one or more peak parameters and the second set of one or more peak parameters are substantially the same. The product ion is further confirmed or determined to be from the analyte and not from a matrix of the sample by correlating the product to a precursor ion of the analyte.

14 Claims, 4 Drawing Sheets (56) References Cited

U.S. PATENT DOCUMENTS

| | | | |
|---|---|---|---|
| 2008/0087809 A1* | 4/2008 | Russ | H01J 49/0027 250/281 |
| 2010/0084547 A1* | 4/2010 | Pringle | H01J 49/428 250/282 |
| 2010/0187414 A1* | 7/2010 | Gorenstein | H01J 49/022 250/282 |
| 2010/0280764 A1* | 11/2010 | Thomson | H01J 49/0009 702/23 |
| 2010/0286927 A1* | 11/2010 | Horn | H01J 49/0036 702/19 |
| 2012/0158318 A1* | 6/2012 | Wright | G01N 30/8675 702/28 |
| 2013/0206979 A1* | 8/2013 | Bonner | H01J 49/0031 250/282 |

* cited by examiner

USE OF VARIABLE XIC WIDTHS OF TOF-MSMS DATA FOR THE DETERMINATION OF BACKGROUND INTERFERENCE IN SRM ASSAYS

CROSS-REFERENCE TO RELATED APPLICATION

This application claims the benefit of U.S. Provisional Patent Application No. 61/493,352 filed Jun. 3, 2011, which is incorporated by reference herein in its entirety.

INTRODUCTION

One difficulty in the development of selected reaction monitoring (SRM) assays is the investigation of the matrix effects and selection of suitable ions for quantification. This is normally performed by the utilization of the quantification methods and investigation of the limit of detection (LOD) and limit of quantitation (LOQ) values to determine the robustness of the assay. Such work can be time consuming and may also not provide a clear picture of the true potential interferences involved. This is due to the inability to define a liquid chromatography (LC) peak shape from low resolution data and the lack of suitable algorithms for the automated analysis of the different elution profiles of the product ions.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
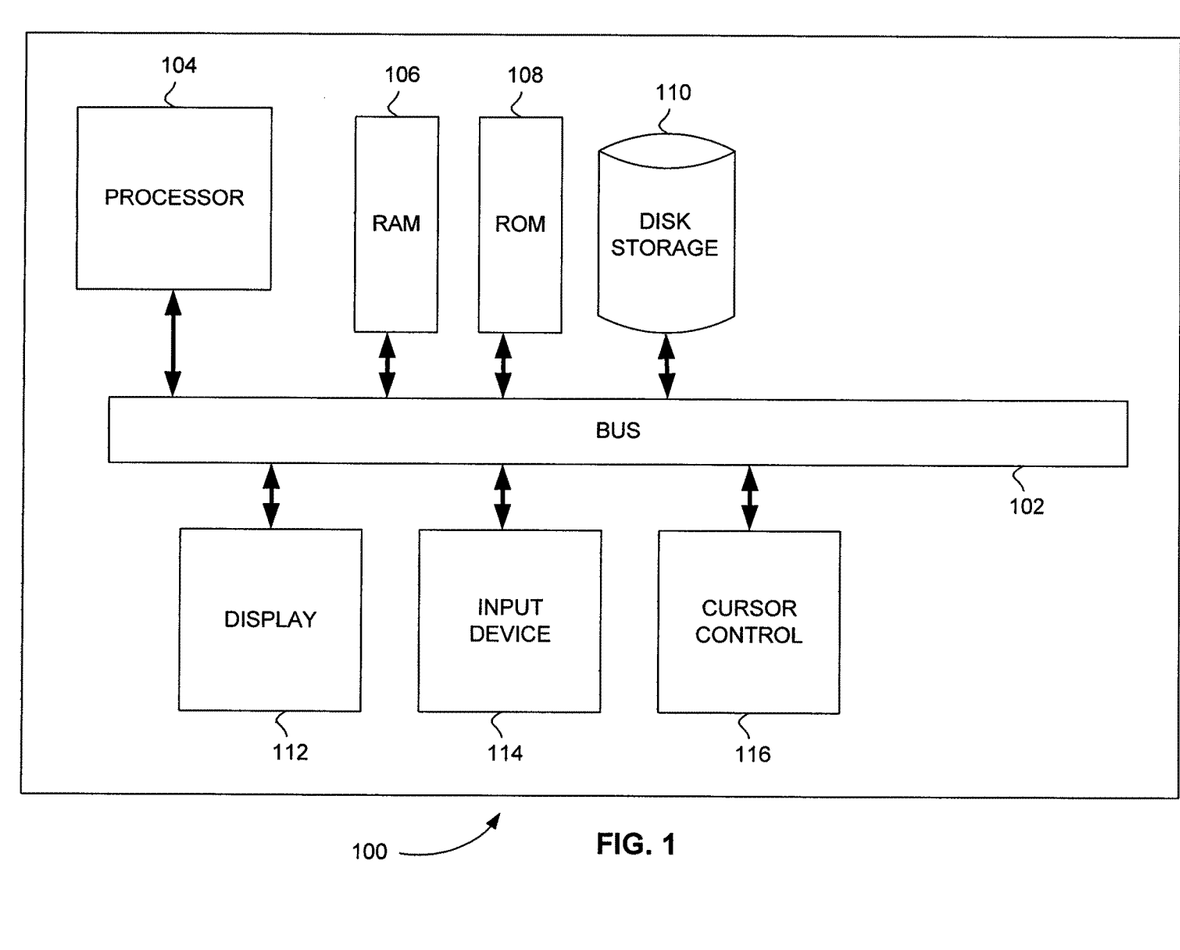
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods of Data Processing

Both qualitative and quantitative information can be obtained from a tandem mass spectrometer. In such an instrument, a precursor ion is selected in a first mass analyzer and fragmented, and the fragments, or product ions, are analyzed in a second analyzer or in a second scan of the first analyzer. The fragment ion spectrum can be used to identify the molecule and the intensity of one or more fragments can be used to quantitate the amount of the compound present in a sample.

Single or selected reaction monitoring (SRM) is a well-known example of this where a precursor ion is selected, fragmented, and passed to a second analyzer, which is set to transmit a single ion. A response is generated when a precursor of the selected mass fragments to give an ion of the selected fragment mass, and this output signal can be used for quantitation. The instrument may be set to measure several fragment ions for confirmation purposes or several precursor-fragment combinations to quantitate different compounds. In multiple reaction monitoring (MRM) a precursor ion is selected, fragmented, and passed to a second analyzer, which is set to transmit two or more ions.

The sensitivity and specificity of an analysis are affected by the width of the mass window selected in the first mass analysis step. Wide windows transmit more ions giving increased sensitivity, but may also allow ions of different mass to pass; if the latter give fragments at the same mass as the target compound interference will occur and the accuracy will be compromised.

In some mass spectrometers the second mass analyzer can be operated at high resolution, allowing the fragment ion window to be narrow so that the specificity can to a large degree be recovered. These instruments also detect all fragments so they are inherently detecting different fragments. With such an instrument it is feasible to use a wide window to maximize sensitivity. Quantitation is achieved by monitoring one or more fragment ions with high resolution, and qualitative analysis can be performed using algorithms that correlate the liquid chromatography (LC) profiles of the fragments with the appropriate precursor masses even though these are not selected directly.

As described above, one difficulty in the development of selected reaction monitoring (SRM) assays is the investigation of the matrix effects and selection of suitable ions for quantification. This work can be time consuming. It may also not provide a clear picture of the true potential interferences between ions. This picture may be obscured due to the inability to define a liquid chromatography (LC) peak shape from low resolution data and the lack of suitable algorithms for the automated analysis of the different elution profiles of the product ions.

In various embodiments, the use of a tandem mass spectrometer with a second mass analyzer that is operated at high resolution allows the investigation of the matrix effects and selection of suitable ions for quantification within a suitable time frame. The high resolution of the fragmentation scan provided by this instrument allows post-acquisition analysis that identifies a precursor/product ion pair of an analyte that is unique from the matrix in the sample. This post-acquisition analysis calculates peak parameters for each product ion of an analyte at high and low extracted ion chromatogram (XIC) resolutions. If the peak parameters at high and low XIC resolutions are substantially the same, the product is uniquely identified from the first matrix. The post-acquisition analysis also confirms or determines that the product ion is from a precursor ion of the analyte.

From this post-acquisition analysis precursor/product ion pairs of an analyte can be found and used in an SRM assay. In addition, by performing multiple physical scans with the tandem mass spectrometer for samples mixed with different matrices coupled with this post-acquisition analysis, precursor/product ion pairs of an analyte can be found that are unique across multiple matrices.

In various embodiments, the use of a tandem mass spectrometer that provides fragmentation scans at multiple mass selection window widths across a mass range allows the investigation of the matrix effects and selection of suitable ions for quantification within a suitable time frame. Typically, fragmentation scans occur at uniform mass selection windows across a mass range. The mass range can include, for example, a preferred mass range of the sample or the entire mass range of the sample. Therefore, the specificity and sensitivity of the entire method analysis are determined by the mass selection window width chosen for the mass analyzer at the start of the analysis.

Recent developments in mass spectrometry hardware have allowed the mass selection window width of a tandem mass spectrometer to be varied or set to any value instead of a single value across a mass range. For example, independent control of both the radio frequency (RF) and direct current (DC) voltages applied to a quadrupole mass filter can allow the selection of variable mass selection window widths. Any type of tandem mass spectrometer can allow the selection of variable mass selection window widths. A tandem mass spectrometer can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, or a Fourier transform mass spectrometer.

Tandem Mass Spectrometry System

Figure 2:
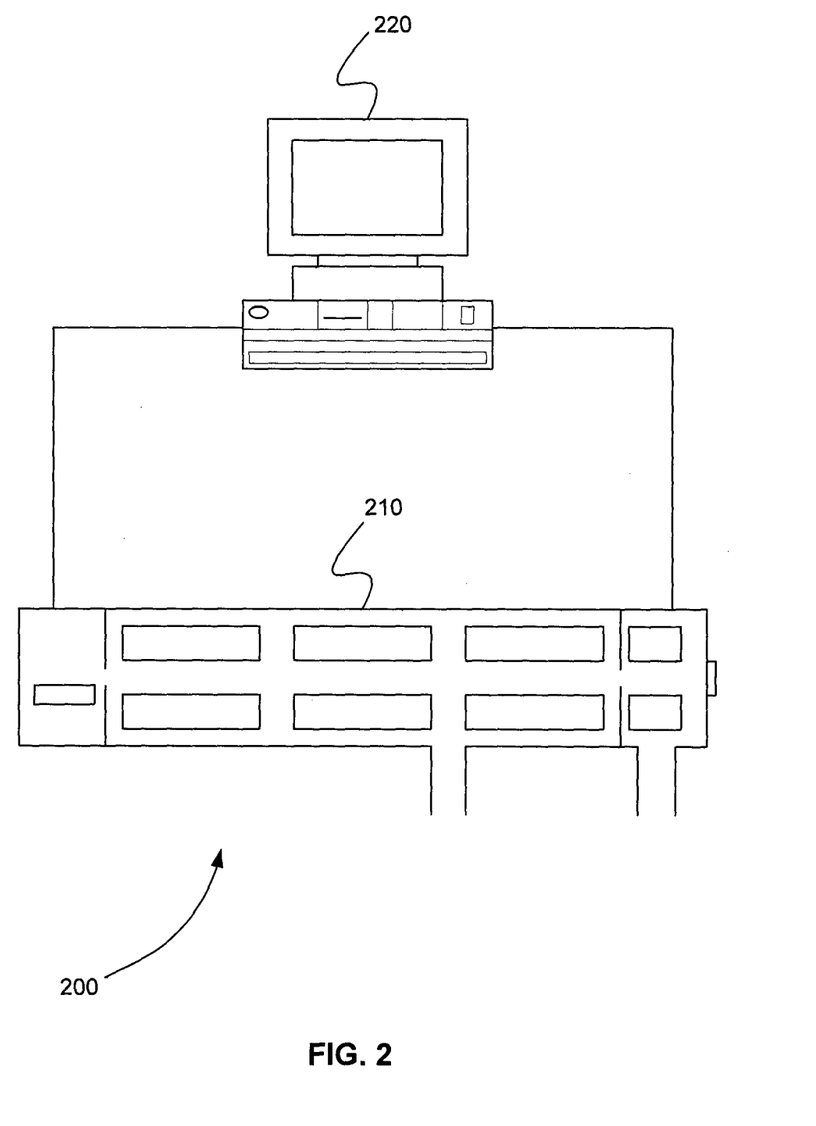
FIG. 2 is a schematic diagram showing a system for identifying a product ion that does not include an interference, in accordance with various embodiments.

FIG. 2 is a schematic diagram showing a system 200 for identifying a product ion that does not include an interference, in accordance with various embodiments. System 200 includes tandem mass spectrometer 210 and processor 220. Processor 220 can be, but is not limited to, a computer, microprocessor, or any device capable of sending and receiving control signals and data from mass spectrometer 210 and processing data.

Tandem mass spectrometer 210 can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, or a Fourier transform mass analyzer. Tandem mass spectrometer 210 can also include a separation device (not shown). The separation device can perform a separation technique that includes, but is not limited to, liquid chromatography, gas chromatography, capillary electrophoresis, or ion mobility. Tandem mass spectrometer 210 can include separating mass spectrometry stages or steps in space or time, respectively.

Tandem mass spectrometer 210 analyzes a first sample that includes a first matrix using one or more precursor scans. Processor 220 is in communication with tandem mass spectrometer 210. Processor 220 receives a first full product ion spectrum for a mass range of an analyte in the first sample from tandem mass spectrometer 210. Processor 220 calculates a first set of one or more peak parameters for a product ion in the first full product ion spectrum using a first XIC window width. Processor 220 calculates a second set of one or more peak parameters for the product ion in the first full product ion spectrum using a second XIC window width. The first XIC window width is narrower than the second XIC window width, for example. Finally, processor 220 identifies the product ion as not including an interference, if the first set of one or more peak parameters and the second set of one or more peak parameters are substantially the same.

In various embodiments, system 200 is used to further uniquely identify a precursor ion and product ion pair of the analyte from a first matrix. The first sample includes the first matrix in addition to the analyte. Processor 220 correlates the product ion to a precursor ion of the analyte in the first sample. Processor 220 identifies the precursor ion and the product ion as being unique from the first matrix, if the first set of one or more peak parameters and the second set of one or more peak parameters are substantially the same, and if the product ion is from the analyte and not from the first matrix.

In various embodiments, tandem mass spectrometer 210 performs a single precursor scan and multiple fragmentation scans at multiple mass selection window widths across a mass range that allow post acquisition processing to be run after a single run of tandem mass spectrometer 210. Tandem mass spectrometer 210 analyzes the first sample using a single mass spectrometry scan of one or more precursor ions and two or more mass spectrometry scans of the product ions using two or more isolation windows widths across the mass range. The two or more isolation windows widths can be uniform or variable.

In various embodiments, tandem mass spectrometer 210 can also be run multiple times followed by post acquisition processing each time. Tandem mass spectrometer 210 analyzes the first sample using two or more mass spectrometry scans of one or more precursor ions.

In various embodiments, the product ion is a known product ion of the analyte. The first set of one or more peak parameters and the second set of one or more peak parameters are calculated to determine if the first matrix is interfering with the product ion. The product ion is correlated with the precursor ion of the analyte to confirm that the product ion is from the analyte and not from the first matrix.

In various embodiments, the product ion is an unknown product ion. The product ion is correlated with the precursor ion of the analyte to determine that the product ion is from the analyte and not the first matrix. The first set of one or more peak parameters and the second set of one or more peak parameters are calculated to determine if the first matrix is interfering with the product ion.

In various embodiments, processor 220 creates a selected reaction monitoring assay that includes the product ion and the precursor ion.

In various embodiments, system 200 can be used to identify a precursor ion and product ion pair of an analyte that is unique across two or more matrices. For example, tandem mass spectrometer 210 can perform a second analysis to determine if the precursor ion and product ion pair found earlier also uniquely identifies the analyte from a second matrix. Tandem mass spectrometer 210 analyzes a second sample that includes the analyte and a second matrix using one or more precursor scans.

Processor 220 receives a second full product ion spectrum for the mass range of the analyte in the second sample from tandem mass spectrometer 210. Processor 220 calculates a third set of one or more peak parameters for the product ion in the second full product ion spectrum using the first XIC window width. Processor 220 calculates a fourth set of one or more peak parameters for the product ion in the second full product ion spectrum using the second XIC window width. Processor 220 correlates the product ion to a precursor ion of the analyte in the second sample. Finally, processor 220 identifies the precursor ion and the product ion as being unique from the first matrix and the second matrix, if the third set of one or more peak parameters and the fourth set of one or more peak parameters are substantially the same, and if the product ion is from the analyte not the second matrix.

The two XIC window widths used across two or more matrices are preferably the same. In various embodiments the two XIC window widths used across two or more matrices can be different.

Tandem Mass Spectrometry Method

Figure 3:
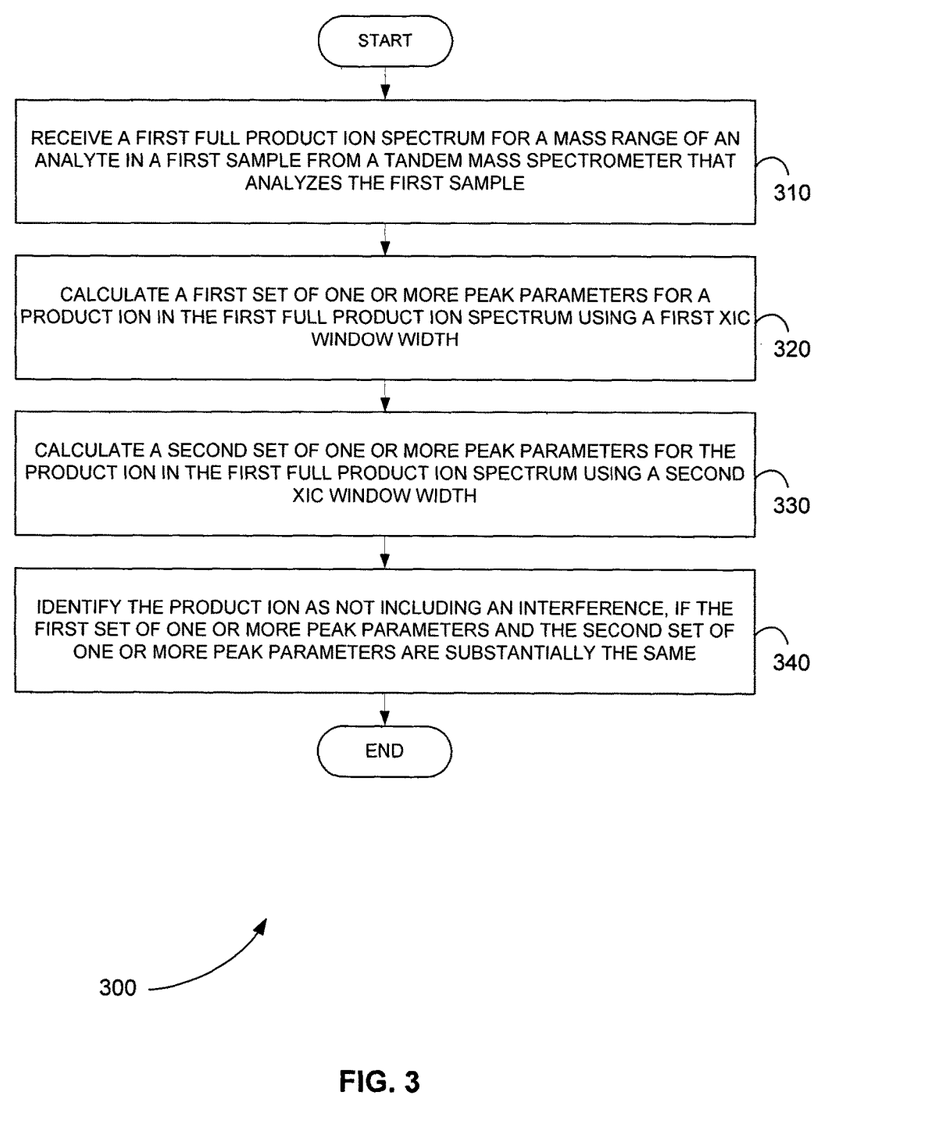
FIG. 3 is an exemplary flowchart showing a method for identifying a product ion that does not include an interference, in accordance with various embodiments.

FIG. 3 is an exemplary flowchart showing a method 300 for identifying a product ion that does not include an interference, in accordance with various embodiments.

In step 310 of method 300, a first full product ion spectrum for a mass range of an analyte in a first sample is received from a tandem mass spectrometer that analyzes the first sample.

In step 320, a first set of one or more peak parameters is calculated for a product ion in the first full product ion spectrum using a first XIC window width.

In step 330, a second set of one or more peak parameters is calculated for the product ion in the first full product ion spectrum using a second XIC window width.

In step 340, the product ion is identified as not including an interference, if the first set of one or more peak parameters and the second set of one or more peak parameters are substantially the same.

Tandem Mass Spectrometry Computer Program Product

In various embodiments, a computer program product includes a tangible computer-readable storage medium whose contents include a program with instructions being executed on a processor so as to perform a method for identifying a product ion that does not include an interference. This method is performed by a system that includes one or more distinct software modules.

Figure 4:
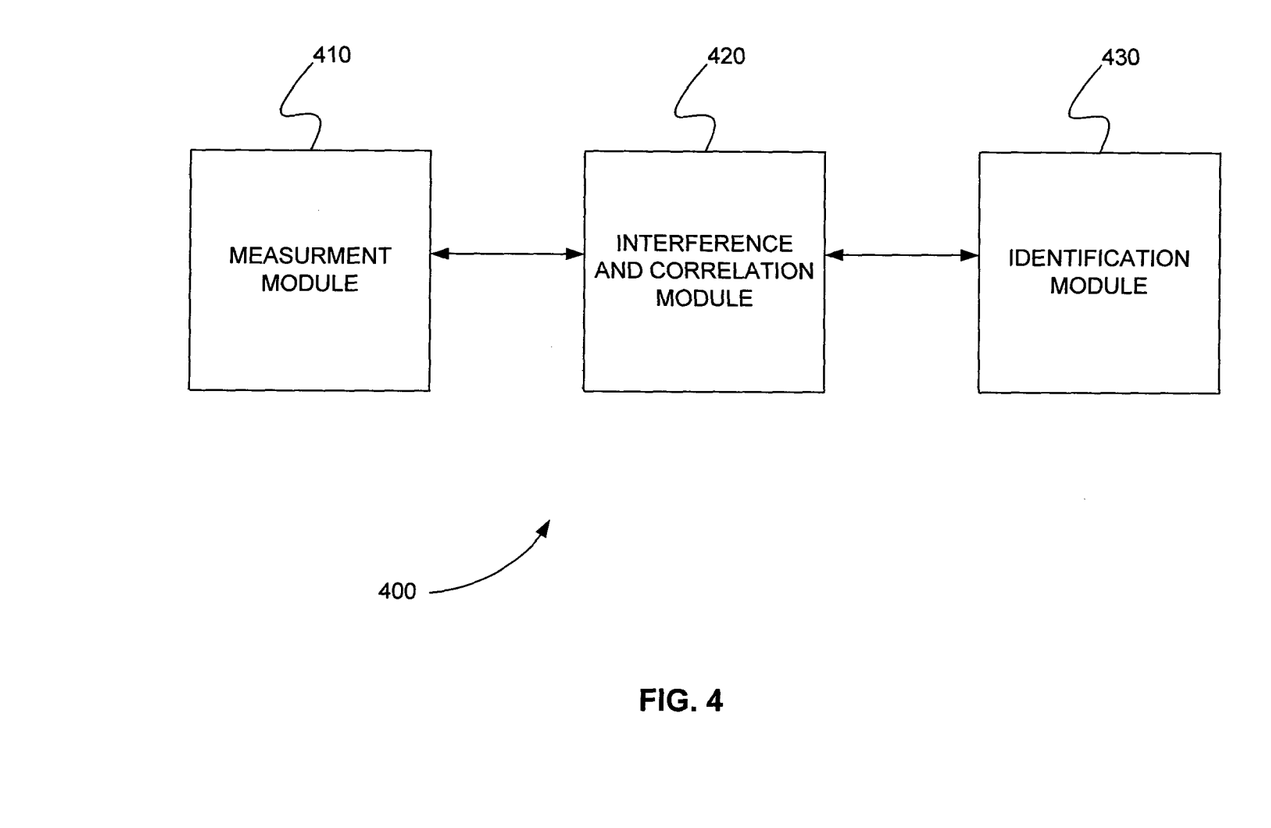
FIG. 4 is a schematic diagram of a system that includes one or more distinct software modules that performs a method for identifying a product ion that does not include an interference, in accordance with various embodiments.

FIG. 4 is a schematic diagram of a system 400 that includes one or more distinct software modules that performs a method for identifying a product ion that does not include an interference, in accordance with various embodiments. System 400 includes measurement module 410, interference and correlation module 420, and identification module 430.

Measurement module 410 receives a first full product ion spectrum for a mass range of an analyte in a first sample from a tandem mass spectrometer that analyzes the first sample. Interference and correlation module 420 calculates a first set of one or more peak parameters for a product ion in the first full product ion spectrum using a first XIC window width. Interference and correlation module 420 calculates a second set of one or more peak parameters for the product ion in the first full product ion spectrum using a second XIC window width using the interference and correlation module. Identification module 430 identifies the product ion as not including an interference, if the first set of one or more peak parameters and the second set of one or more peak parameters are substantially the same using the identification module.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying a product ion that does not include an interference, comprising:
   a separation device that separates a first sample that includes an analyte over time;
   a tandem mass spectrometer that performs a single precursor ion scan of a mass range of the first sample using two or more precursor ion isolation windows with variable widths and performs fragmentation scans of the two or more precursor ion isolation windows with variable widths each time the first sample is separated producing a full product ion spectrum of each of the two or more precursor ion isolation windows, wherein the tandem mass spectrometer includes a quadrupole mass filter that allows selection of the two or more precursor ion isolation windows with variable widths and wherein the quadrupole mass filter selects the two or more precursor ion isolation windows with variable widths to investigate matrix effects of the first sample and to allow the selection of suitable ions for quantification within a suitable time frame; and
   a processor in communication with the tandem mass spectrometer that
      independently controls both the radio frequency (RF) and direct current (DC) voltages applied to the quadrupole mass filter to allow the selection of the two or more precursor ion isolation windows with variable widths each time the first sample is separated;
      receives a full product ion spectrum for each of the two or more precursor ion isolation windows each time the first sample is separated from the tandem mass spectrometer,
      calculates a first set of one or more peak parameters for a product ion in the full product ion spectra of a precursor ion isolation window of the two or more precursor ion isolation windows using a first extracted ion chromatogram window width,
      calculates a second set of one or more peak parameters for the product ion in the full product ion spectra of the precursor ion isolation window of the two or more precursor ion isolation windows using a second extracted ion chromatogram window width, and
      identifies the product ion as not including an interference, if the first set of one or more peak parameters and the second set of one or more peak parameters are substantially the same.

2. The system of claim 1, wherein the first sample includes a first matrix in addition to the analyte and the processor
   correlates the product ion to a precursor ion of the analyte in the first sample, and
   identifies the precursor ion and the product ion as being unique from the first matrix, if the first set of one or more peak parameters and the second set of one or more peak parameters are substantially the same, and if the product ion is from the analyte and not from the first matrix.

3. The system of claim 2, wherein the product ion is a known product ion of the analyte, the first set of one or more peak parameters and the second set of one or more peak parameters are calculated to determine if the first matrix is interfering with the product ion, and the product ion is correlated with the precursor ion of the analyte to confirm that the product ion is from the analyte and not from the first matrix.

4. The system of claim 2, wherein the product ion is an unknown product ion, the product ion is correlated with the precursor ion of the analyte to determine that the product ion is from the analyte and not the first matrix, and the first set of one or more peak parameters and the second set of one or more peak parameters are calculated to determine if the first matrix is interfering with the product ion.

5. The system of claim 2, wherein
   the separation device separates a second sample that includes the analyte and a second matrix over time,
   the tandem mass spectrometer performs a single precursor scan of a mass range of the second sample using two or more precursor ion isolation windows with variable widths and performs fragmentation scans of the two or more precursor ion isolation windows with variable widths each time the second sample is separated producing a full product ion spectrum of each of the two or more precursor ion isolation windows,
   and the processor
      independently controls both the radio frequency (RF) and direct current (DC) voltages applied to the quadrupole mass filter to allow the selection of the two or more precursor ion isolation windows with variable widths each time the second sample is separated, receives a full product ion spectrum for each of the two or more precursor ion isolation windows each time the second sample is separated from the tandem mass spectrometer, calculates a third set of one or more peak parameters for the product ion in the full product ion spectra of a precursor ion isolation window of the two or more precursor ion isolation windows using the first extracted ion chromatogram window width, calculates a fourth set of one or more peak parameters for the product ion in the full product ion spectra of the precursor ion isolation window of the two or more precursor ion isolation windows using the second extracted ion chromatogram window width, correlates the product ion to a precursor ion of the analyte in the second sample, and identifies the precursor ion and the product ion as being unique from the first matrix and the second matrix, if the third set of one or more peak parameters and the fourth set of one or more peak parameters are substantially the same, and if the product ion is from the analyte not the second matrix.

6. The system of claim 1, wherein the first extracted ion chromatogram window width is narrower than the second extracted ion chromatogram window width.

7. The system of claim 1, wherein the processor creates a selected reaction monitoring assay that includes the product ion and the precursor ion.

8. A method for identifying a product ion that does not include an interference, comprising:

separating a first sample that includes an analyte over time using a separation device;

performing a single precursor ion scan of a mass range of the first sample using two or more precursor ion isolation windows with variable widths and performing fragmentation scans of the two or more precursor ion isolation windows with variable widths each time the first sample is separated producing a full product ion spectrum of each of the two or more precursor ion isolation windows using a tandem mass spectrometer, wherein the tandem mass spectrometer includes a quadrupole mass filter that allows selection of the two or more precursor ion isolation windows with variable widths and wherein the quadrupole mass filter selects the two or more precursor ion isolation windows with variable widths to investigate matrix effects of the first sample and to allow the selection of suitable ions for quantification within a suitable time frame;

independently controlling both the radio frequency (RF) and direct current (DC) voltages applied to the quadrupole mass filter to allow the selection of the two or more precursor ion isolation windows with variable widths each time the first sample is separated using a processor;

receiving a full product ion spectrum for each of the two or more precursor ion isolation windows each time the first sample is separated from a tandem mass spectrometer using the processor;

calculating a first set of one or more peak parameters for a product ion in the full product ion spectra of a precursor ion isolation window of the two or more precursor ion isolation windows using a first extracted ion chromatogram window width using the processor;

calculating a second set of one or more peak parameters for the product ion in the full product ion spectra of the precursor ion isolation window of the two or more precursor ion isolation windows using a second extracted ion chromatogram window width using the processor; and identifying the product ion as not including an interference, if the first set of one or more peak parameters and the second set of one or more peak parameters are substantially the same using the processor.

9. The method of claim 8, wherein the first sample includes a first matrix in addition to the analyte and further comprising correlating the product ion to a precursor ion of the analyte in the first sample, and identifying the precursor ion and the product ion as being unique from the first matrix, if the first set of one or more peak parameters and the second set of one or more peak parameters are substantially the same, and if the product ion is from the analyte and not from the first matrix.

10. The method of claim 9, wherein the product ion is an unknown product ion, the product ion is correlated with the precursor ion of the analyte to determine that the product ion is from the analyte and not the first matrix, and the first set of one or more peak parameters and the second set of one or more peak parameters are calculated to determine if the first matrix is interfering with the product ion.

11. The method of claim 9, wherein the product ion is a known product ion of the analyte, the first set of one or more peak parameters and the second set of one or more peak parameters are calculated to determine if the first matrix is interfering with the product ion, and the product ion is correlated with the precursor ion of the analyte to confirm that the product ion is from the analyte and not from the first matrix.

12. The method of claim 8, wherein the first extracted ion chromatogram window width is narrower than the second extracted ion chromatogram window width.

13. The method of claim 8, wherein the processor creates a selected reaction monitoring assay that includes the product ion and the precursor ion.

14. A computer program product, comprising a non-transitory tangible computer-readable storage medium whose contents include a program with instructions being executed on a processor so as to perform a method for identifying a product ion that does not include an interference, the method comprising:

providing a system, wherein the system comprises one or more distinct software modules, and wherein the distinct software modules comprise a measurement module, an interference and correlation module, and an identification module;

instructing a separation device to separate a first sample that includes an analyte over time using the measurement module:

instructing a tandem mass spectrometer to perform a single precursor ion scan of a mass range of the first sample using two or more precursor ion isolation windows with variable widths and performs fragmentation scans of the two or more precursor ion isolation windows with variable widths each time the first sample is separated producing a full product ion spectrum of each of the two or more precursor ion isolation windows using the measurement module, wherein the tandem mass spectrometer includes a quadrupole mass filter that allows selection of the two or more precursor ion isolation windows with variable widths and wherein the quadrupole mass filter selects the two or more precursor ion isolation windows with variable widths to investigate matrix effects of the first sample and to allow the selection of suitable ions for quantification within a suitable time frame;

independently controlling both the radio frequency (RF) and direct current (DC) voltages applied to the quadrupole mass filter to allow the selection of the two or more precursor ion isolation windows with variable widths each time the first sample is separated using the measurement module;

receiving a first full product ion spectrum for each of the two or more precursor ion isolation windows each time the first sample is separated for a mass range of an analyte in a first sample from a tandem mass spectrometer that analyzes the first sample using the measurement module;

calculating a first set of one or more peak parameters for a product ion in the first full product ion spectraum of a precursor ion isolation window of the two or more precursor ion isolation windows using a first extracted ion chromatogram window width using the interference and correlation module;

calculating a second set of one or more peak parameters for the product ion in the first full product ion spectraum of the precursor ion isolation window of the two or more precursor ion isolation windows using a second extracted ion chromatogram window width using the interference and correlation module; and identifying the product ion as not including an interference, if the first set of one or more peak parameters and the second set of one or more peak parameters are substantially the same using the identification module.

\* \* \* \* \*